United States Patent
Schwartz (12)

(10) Patent No.: US 6,319,899 B1
(45) Date of Patent: Nov. 20, 2001

(54) METHOD AND COMPOSITION FOR THE TREATMENT OF INFLAMMATORY BOWEL DISEASE

(75) Inventor: Marshall Z. Schwartz, Bryn Mawr, PA (US)

(73) Assignee: The Nemours Foundation, Jacksonville, FL (US)

( * ) Notice: Subject to any disclaimer, the term of this patent is extended or adjusted under 35 U.S.C. 154(b) by 0 days.

(21) Appl. No.: 09/395,129

(22) Filed: Sep. 14, 1999

Related U.S. Application Data

(63) Continuation-in-part of application No. 08/932,391, filed on Sep. 17, 1997.

(51) Int. Cl.⁷ ............................ A61K 38/16; A61K 38/18
(52) U.S. Cl. ................................... 514/12; 514/2
(58) Field of Search ............................ 514/2, 12

(56) References Cited

U.S. PATENT DOCUMENTS 6,051,557 * 4/2000 Drucker ................................. 514/12

FOREIGN PATENT DOCUMENTS

08231418 * 2/1995 (JP).

OTHER PUBLICATIONS

Zushi et al. Am. J. Physiol.270, G757–G762, Feb. 1996.*
Halttunen, T. et al Gastroenterology, 111, 1252–1262, Nov. 1996.*

"Importance of fibroblastic support for in vitro differentiation of intestinal endodhermal cells and for their response to glucocorticoids," by M. Kedinger, P. Simon–Assmann, E. Alexandre and K. Haffen, *Cell Differentiation*, 20 (1987) 171–182.

"Primary Cultures for Studies of Cell Regulation and Physiology in Intestinal Epithelium," by G. S. Evans, N. Flint, and C. S. Potten, *Annu. Rev. Physiol.*. (1994) 56: 399–417.

"The development of a method for the preparation of rat intestinal epithelial cell primary cultures," by G. S. Evans, N. Flint, A. S. Somers, B. Eyden and C. S. Potten, *Journal of Cell Science*, 101 (1992) 219–231.

"Iron Absorption; Characterization of isolated duodenal epithelial cells along a crypt–villus axis in rats fed diets with different iron content," by Phillip S. Oates, Carla Thomas and Evan H. Morgan, *Journal of Gastroenterology and Hepatology* (1997) 12: 829–838.

\* cited by examiner

*Primary Examiner*—Michael Borin
(74) *Attorney, Agent, or Firm*—McGuireWoods LLP

(57) ABSTRACT

The present invention relates to a method and composition for treating a patient having a condition characterized as inflammatory bowel disease with an effective dose of HGF. Mucosal damage and histologic lesions are reduced by administering HGF to patients suffering from the same. HGF may be administered to the patient lumenally or systemically.

8 Claims, No Drawings

METHOD AND COMPOSITION FOR THE TREATMENT OF INFLAMMATORY BOWEL DISEASE

This application is a continuation-in-part of application Ser. No. 08/932,391, filed on Sep. 17, 1997, now U.S. Pat. No. 5,972,887.

BACKGROUND OF THE INVENTION

The present invention relates broadly to the treatment of inflammatory bowel diseases in a patient. More particularly, the invention relates to treating a patient having an inflammatory bowel disease condition with Hepatocyte Growth Factor ("HGF").

Chronic Ulcerative Colitis ("CUC") and Crohn's Disease ("CD"), generally referred to as Inflammatory Bowel Disease ("IBD"), are devastating disorders with an unknown etiology. Current medical therapy can control symptomatic exacerbations of IBD, but does not provide a cure. Progress in understanding the pathogenesis of IBD has been slowed by the lack of availability of animal models that exhibit the chronic, spontaneous, relapsing gastrointestinal ("GI") inflammation that is symptomatic of human IBD. Numerous murine and rat experimental models exist that possess some but not all of the features of human IBD.

A study has shown that the introduction of HLA-B27 and human $\beta_2$-microglobulin genes into Fisher (F344) rats induces spontaneous chronic GI inflammation. Hammer et al., *Cell* 63: 1099–1112 (1990). In this model, rats spontaneously develop a chronic inflammatory disease that includes most of the clinical and pathologic features of the B27-associated disorders in humans. The most prevalent site of inflammation in these transgenic rats appears to be localized to the gastro-intestinal tract, and the most persistent finding is diarrhea developing in 100% of the animals at 20 weeks of age. Hammer et al., *Cell* 63: 1099–1112 (1990); Elson et al., *Gastroenterology* 109: 1344–1367 (1995). Because it closely approximates the human disease, as will be described in detail below, this transgenic rat model was used to study the therapeutic benefit of HGF as a treatment for IBD.

In a previous application, application Ser. No. 08/932, 391, filed on Sep. 17, 1997, herein specifically incorporated by reference, HGF was shown to increase the intestinal absorptive functions and increase the intestinal tissue mass of the small intestine beyond the normal adaptive response in subjects suffering from Short Bowel Syndrome, a surgical resection of the small intestine or other developmental abnormalities of the small intestine. The subject of the present invention relates to the therapeutic benefits of treating subjects with HGF who are suffering from inflammation of the bowel as in IBD.

SUMMARY OF THE INVENTION

The present invention relates to a method for treating a patient comprising administering an effective dose of HGF wherein the patient has a condition characterized as inflammatory bowel disease.

The condition may be selected from the group consisting of Chronic Ulcerative Colitis, Crohn's Disease, necrotizing enterocolitis, severe acute gastroenteritis, chronic gastroenteritis, cholera, chronic infections of the bowel, immunologic disorders affecting the small intestine, immunodeficiency syndromes affecting the small intestine, and HIV.

Further, the invention relates to a method for treating a patient having intestinal mucosal damage comprising decreasing the mucosal damage of the small intestine by administering an effective dose of HGF to the patient.

Still further, the invention relates to a method for treating a patient having histologic lesions comprising decreasing the histologic lesions of the small intestine by administering an effective dose of HGF to the patient.

Further, the invention includes the systemic lumenal administration of HGF to a patient. The effective dosage range of HGF for the patient is about 30 µg/kg body weight/day to about 300 µg/kg body weight/day. Preferably, the effective dose of HGF is about 150 µg/kg body weight/day.

Further, the invention relates to a composition for treating a patient having a condition characterized as inflammatory bowel disease comprising an effective dose of HGF in a suitable carrier. The suitable carrier may be selected from the group consisting of intravenous fluid and sustained release enteral preparations.

DETAILED DESCRIPTION OF THE PREFERRED EMBODIMENT

It has been discovered that HGF is useful for treating patients suffering from IBD. As used herein, Inflammatory Bowel Disease or IBD includes not only Chronic Ulcerative Colitis ("CUC") and Crohn's Disease ("CD") but includes necrotizing enterocolitis, severe acute gastroenteritis, chronic gastroenteritis, cholera, as well as other chronic infections of the bowel.

Importantly, it has been discovered that administering HGF to subjects characterized as having IBD reduces the gross and histologic lesions in these subjects. Further, HGF reduces the gene expression of inflammatory mediators such as TNF-$\alpha$ and INF-$\gamma$ in these subjects.

It will be appreciated that the present invention will also have application for treating intestinal disorders in subjects having immunologic disorders and immunodeficiency syndromes such as HIV and the like.

HGF can be administered to patients at effective doses and for effective periods of time by the intestinal intralumenal route either by catheter or sustained release preparations or by a systemic route including but not limited to intravenous administration. Suitable carriers for HGF may be found in Remington's Pharmaceutical Sciences, $18^{th}$ ed., 1990, Mack Publishing Co., Easton, Pa. An effective dose of HGF is that amount of HGF administered to a subject having an IBD condition that is sufficient to reduce gross or histologic lesions in the intestine of the subject. Preferably, the effective dose of HGF is between about 30 µg/kg body weight/day and about 300 µg/kg body weight/day. Most preferably, the effective dose of HGF is about 150 µg/kg body weight/day. Subjects or patients include, but are not limited to, rats, animals, and humans.

The following is designed merely to provide exemplification of the preferred embodiments of the invention, and should not be construed as providing any limitation on the scope of the invention which is described in the specification and the appended claims.

Five adult Fisher 344 (F344) rats (Harlan Sprague-Dawley, Indianapolis, Ind.) and 9 adult HLA-B27 rats (Taconic Transgenic Division, Germantown, N.Y.) aged 20–24 weeks were studied. Five HLA-B27 rats underwent placement of a jugular venous catheter connected to a subcutaneously placed osmotic pump (model 2002, Alza Corp., Palo Alto, Calif.). Rats were divided into three groups: Group 1 contained five (5) normal F344 rats receiving no treatment; Group 2 contained four (4) F344-HLA-B27 rats receiving no treatment; and Group 3 contained five (5) F344-HLA-B27 rats receiving HGF at 150 μg/kg body weight/day. Recombinant human HGF was provided by the Mitsubishi Chemical Corporation. After 14 days, the rats were sacrificed and the gastro-intestinal tract, from the Ligament of Treitz to the rectum, was resected and opened along its antimesenteric border. Total mucosal damage (expressed as % surface area damaged) was measured using Image Analysis Software (Sigmascan 2.0).

With reference now to Table I, the mucosal damage, histologic lesion scores are shown for each of the three groups of rats. Group 1 consists of F344 rats, while Group 2 consists of HLA-B27 rats receiving no treatment and Group 3 consists of HLA-B27 rats receiving HGF at 150 μg/kg body weight/day. The mucosal damage and histologic lesion scores are determined by methods well known to those skilled in the art. The F344 rats of Group 1 did not demonstrate evidence of gross or histologic lesions in the small or large intestine. As can be seen in Table I, the administration of HGF significantly reduced the gross (90% decrease, $p<0.01$) and histologic (53% decrease, $p<0.01$) lesions in the Group 3 rats (HLA-B27+HGF) when compared to the rats in Group 2 (HLA-B27) that did not receive HGF.

The RNA concentration and purity were determined by measuring the absorbency at 260 and 280 nm. One microgram of total RNA was reverse-transcribed and the cDNA sequence was amplified using the following primers: Tumor Necrosis Factor-α (TNF-α); Interferon-γ (INF-γ); Interleukin-2 (IL-2); and glyceraldehyde-3-phosphate dehydrogenase (GAPDH)—the intestinal standard. The temperature profile of the PCR reactions consisted of a 2 minute melting step at 95° C., then 25 cycles of 30 seconds at 94° C., 30 seconds at 63° C., and 1 minute at 75° C., followed by a final extension step of 5 minutes at 65° C. Independent experiments established that 25 cycles were within the linear range of the multiplex PCR assay. RT/PCR products were separated by size on a 4% agarose gel and stained with ethidium bromide. Images were transferred to an Apple Macintosh Quadra 800 via an Eagle Eye still video imaging system and the relative band intensities were analyzed using NIH image analysis software. Statistical analysis was performed using Student's t-test and expressed as mean±SEM.

Table I shows the mean band intensities for TNF-α, INF-γ, and IL-2 for each of the three groups of rats. The administration of HGF significantly reduced the gene expression of the inflammatory mediators, TNF-α(52% decrease, $p<0.01$) and INF-γ (93% decrease, $p<0.01$) in Group 3 when compared to rats in Group 2. IL-2 gene expression was not detectable in any of the groups.

The present invention demonstrates that HGF reduces the gross and histologic intestinal lesions normally present in transgenic rats when compared to non-treated animals. This beneficial effect is supported by a reduction in the gene expression of the inflammatory mediators TNF-α and INF-γ.

Those persons skilled in the art will therefore readily understand that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

TABLE I

| Groups | Mucosal Damage (%) | Histologic Lesion Score | Mean Band Intensity | | |
|---|---|---|---|---|---|
| | | | TNF-α/ GAPDH | INF-γ/ GAPDH | IL-2/ GAPDH |
| 1 | 0.0 | 0.4 ± 025 | 0.0 | 0.0 | 0.0 |
| 2 | 8.5 ± 0.96 | 6.0 ± 0.41 | 0.8 ± 0.07 | 0.67 ± 0.12 | 0.0 |
| 3 | 0.85 ± 0.85** | 2.8 ± 0.5** | 0.4 ± 0.05** | 0.05 ± 0.03** | 0.0 |

**$p < 0.01$

What is claims is:

1. A method for treating a patient having a condition characterized as inflammatory bowel disease comprising reducing cytokine inflammatory mediator activity by administering a dose of HGF effective to reduce the gene expression of cytokine inflammatory mediators.

2. The method of claim 1 wherein a patient has a condition selected from the group consisting of Chronic Ulcerative Colitis, Crohn's Disease, necrotizing enterocolitis, severe acute gastroenteritis, chronic gastroenteritis, cholera, chronic infections of the bowel, immunologic disorders affecting the small intestine, and immunodeficiency syndromes affecting the small intestine.

3. The method of claim 1 wherein the administration of HGF is performed systemically.

4. The method of claim 1 wherein the administration of HGF is performed lumenally.

5. The method of claim 1 wherein the effective dosage range of HGF is between about 30 μg/kg body weight/day to about 300 μg/kg body weight/day.

6. The method of claim 1 wherein the effective dose of HGF is about 150 μg/kg body weight/day.

7. The method of claim 1 wherein the cytokine inflammatory mediators are selected from the group consisting of TNF-α, INF-γ, and combinations thereof.

8. The method of claim 1 wherein the reduction of gene expression of cytokine inflammatory mediators results in a reduction in inflammation in the small bowel and colon.

* * * * *

UNITED STATES PATENT AND TRADEMARK OFFICE
CERTIFICATE OF CORRECTION

PATENT NO. : 6,319,899 B1  
DATED : November 13, 2001  
INVENTOR(S) : Jahangir Rastegar et al.

It is certified that error appears in the above-identified patent and that said Letters Patent is hereby corrected as shown below:

<u>Title page,</u>  
Item [73], Assignee, change "Omitek Research and Development Inc., New York, NY" to -- Omnitek Research and Development Inc., Brooklyn, NY --.

Signed and Sealed this

Sixth Day of August, 2002

Attest:

Attesting Officer

JAMES E. ROGAN  
*Director of the United States Patent and Trademark Office*

UNITED STATES PATENT AND TRADEMARK OFFICE
CERTIFICATE OF CORRECTION

PATENT NO. : 6,319,899 B1
DATED : November 13, 2001
INVENTOR(S) : Jahangir Rastegar et al.

It is certified that error appears in the above-identified patent and that said Letters Patent is hereby corrected as shown below:

<u>Title page,</u>
Item [73], Assignee, change "Omitek Research and Development Inc., New York, NY" to -- Omnitek Research and Development Inc., Brooklyn, NY --.

Signed and Sealed this

Thirteenth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,319,899 B1
DATED        : November 20, 2001
INVENTOR(S)  : Marshall Z. Schwartz It is certified that error appears in the above-identified patent and that said Letters Patent is hereby corrected as shown below:

This certificate supersedes Certificate of Correction issued August 6, 2002 and August 13, 2002 the number was erroneously mentioned and should be vacated since no Certificate of Correction was granted.

Signed and Sealed this

Tenth Day of December, 2002

JAMES E. ROGAN
*Director of the United States Patent and Trademark Office*